United States Patent [19]

Matsumoto et al.

[11] Patent Number: 5,248,819

[45] Date of Patent: Sep. 28, 1993

[54] PROCESS FOR RECOVERING METHACROLEIN

[75] Inventors: Syoichi Matsumoto; Masatoshi Ueoka, both of Himeji; Yosuke Ogata, Hyogo; Hiroshi Yoshida, Toyonaka; Masao Baba, Himeji, all of Japan

[73] Assignee: Nippon Shokubai Kagaku Ogyo Co., Ltd., Osaka, Japan

[21] Appl. No.: 770,142

[22] Filed: Oct. 3, 1991

Related U.S. Application Data

[63] Continuation of Ser. No. 359,228, May 31, 1989, abandoned.

Foreign Application Priority Data

Mar. 6, 1988 [JP] Japan .................... 63-135625

[51] Int. Cl.$^5$ .............. C07C 51/16; C07C 51/235; C07C 51/42
[52] U.S. Cl. ................ 562/532; 562/538; 562/545; 562/599; 562/600
[58] Field of Search ........... 562/532, 538, 545, 599, 562/600

[56] References Cited

U.S. PATENT DOCUMENTS

| | | | |
|---|---|---|---|
| 3,957,880 | 5/1976 | Sato et al. | 203/42 X |
| 4,147,721 | 4/1979 | Leacock | 562/532 |

FOREIGN PATENT DOCUMENTS

| | | |
|---|---|---|
| 0002382 | 6/1979 | European Pat. Off. |
| 2400260 | 3/1979 | Fed. Rep. of Germany |
| 2842092 | 4/1979 | Fed. Rep. of Germany |
| 62-96447 | 10/1985 | Japan |

OTHER PUBLICATIONS

Japanese Abstract 62-96447, vol. 11, No. 307(C-450)(2754) (1987).

*Primary Examiner*—Paul F. Shaver
*Assistant Examiner*—Joseph Conrad, III
*Attorney, Agent, or Firm*—Sherman and Shalloway

[57] ABSTRACT

In the production of methacrylic acid by the vapor phase catalytic oxidation of isobutylene, t-butanol, methacrolein isobutyl aldehyde or isobutyric acid, or mixture thereof, the reaction product gas is condensed by contact with an aqueous phase containing methacrylic acid and acetic acid thereby forming an aqueous solution of methacrylic acid and a gas phase containing methacrolein and methacrylic acid. The aqueous solution of methacrylic acid is extracted with a saturated hydrocarbon solvent containing from 6-9 carbon atoms. The methacrylic acid is extracted into the solvent phase and an aqueous phase containing acetic acid is also formed. Methacrolein is recovered from the gas containing methacrolein and methacrylic acid by contacting the gas with an aqueous phase containing methacrylic acid and acetic acid. An aqueous phase containing methacrylic acid, acetic acid and methacrolein is formed in the methacrolein recovery step. This aqueous phase is contacted with a molecular oxygen containing gas to desorb methacrolein into a gas containing methacrylic acid and methacrolein and also forming an aqueous phase containing methacrylic acid and acetic acid. This aqueous phase is recycled to either or both of the methacrylic acid condensation step and the methacrolein recovery step. Methacrylic acid is recovered from the gas containing methacrylic acid and methacrolein produced in the methacrolein desorption step by mixing this gas with an aqueous phase containing acetic acid recovered from the methacrylic acid extraction step (C). This results in a gas-containing methacrolein which is recycled to the vapor phase reaction.

4 Claims, 2 Drawing Sheets

PROCESS FOR RECOVERING METHACROLEIN

This application is a continuation of application Ser. No. 07/359,228, filed May 31, 1989, now abandoned.

Many industrial catalysts have been developed for the production of methacrylic acid by catalytic oxidation reaction of isobutylene, t-butanol, methacrolein, isobutyl aldehyde or isobutyric acid (hereinafter referred to as "isobutylene and the like") in a vapor phase. However, a catalyst having an industrially sufficiently satisfactory performance has not been found yet. Because of this, the catalytic oxidation reaction is ordinarily carried out while the conversion of methacrolein, an intermediate reaction product or a reaction material, is controlled to 50 to 80%, and from the resulting reaction product gas, methacrylic acid is separated and refined to obtain a methacrylic acid product, on the other hand, methacrolein is recovered and circulated in the reaction system to be re-used.

This invention provides a method of industrially advantageously recovering methacrolein for circulating and re-using methacrolein in the production of methacrylic acid by such a catalytic oxidation reaction in a vapor phase.

Heretofore, the production of methacrylic acid by the catalytic oxidation reaction of isobutylene and the like in a vapor phase has been carried out as follows. Namely, isobutylene and the like are subjected to a catalytic oxidation reaction in a vapor phase, and the resulting gas as a reaction product is brought into contact with water in a methacrylic acid condensation column to obtain an aqueous solution of methacrylic acid, bringing said aqueous solution into contact with a solvent in a methacrylic acid extraction column to extract methacrylic acid, which is separated and further introduced to a refining step to obtain a methacrylic acid product.

The gas after being brought into contact with water contains methacrolein, the recovery and re-use of said methacrolein is carried out by introducing said gas to a methacrolein absorption column where it is brought into contact with water, the resulting aqueous solution of methacrolein is introduced to a methacrolein desorption column where methacrolein is desorbed and recovered, and then returned to the reaction system. However, methacrolein has a small solubility in water and for the absorption of methacrolein, it is necessary to use a large amount of water or use a multi-stage absorption column. Further, a large amount of waste water is discharged, which possesses a problem of how to dispose of it. Accordingly, a proposal is made to use an organic solvent besides water as an absorption solvent in a methacrolein absorption column. This proposed method, however, possesses another problem that in concomitance with circulation and re-use of methacrolein after it is separated and recovered in the oxidation reaction system, said organic solvent is circulated in the oxidation reaction system together with the recovered methacrolein, and the circulating organic solvent tends to poison the catalyst. Hence, this is not a preferable method.

In the event that methacrylic acid is contained in the recovered methacrolein, due to polymerization of methacrylic acid in the reaction system, lowering of the yield and clogging attributable to the polymer and lowering of the catalytic activity of the catalyst are likely to be caused, which obstruct the continuous operation. Accordingly, in the methacrylic acid condensation column, an attention should be paid to ensure that methacrylic acid be sufficiently collected there and the gas going out from said collection column be free from methacrylic acid, which compels the use of a high-performance separator or an additional or extra amount of water, which is industrially inconvenient.

On the other hand, an aqueous solution of methacrylic acid obtained in the methacrylic acid condensation column is separated in the methacrylic acid extraction column by the use of a solvent to a solvent phase containing methacrylic acid and an aqueous solution phase, from the former, by further passing through a refining step, a methacrylic acid product is obtained, while the latter is disposed of as waste water. In such a process, a very large amount of water is used, in addition, a large amount of waste water is produced.

For example, British Patent No. 2,004,886 discloses a process for efficiently recovering methacrolein which comprises using part of an aqueous solution of methacrylic acid discharged from a methacrylic acid condensation column as an absorption solution to be fed to a methacrolein absorption column, feeding an aqueous solution after having absorbed methacrolein to a methacrolein desorption column, feeding an inert gas from the lower portion of said desorption column and separating methacrolein from the top portion of said desorption column and separating methacrylic acid from the bottom portion of said desorption column. However, according to this process, because methacrylic acid stripps from the top portion of the methacrolein desorption column, this process possesses problems such as lowering of the yield, an adverse effect on the oxidation catalyst and discharge of a large amount of waste water. Further, because an aqueous solution of methacrylic acid discharged from the methacrylic acid condensation column is directly used as an absorption solvent, a high boiling point by-product contained in said aqueous solution brings about a soil in the methacrolein absorption column, which makes it difficult to continuously operate the reaction for a long period of time, which is a fatal defect as an industrial process for the production.

In U.S. Pat. No. 4,618,709, upon obtaining methacrylic acid by a vapor-phase oxidation of methacrolein, by the use of a non-condensable gas as the majority of an inert gas, the concentration of an aqueous solution of methacrylic acid is elevated and the amount of waste water is reduced to facilitate the disposal of waste water. In this case also, the amount of waste water is reduced to be sure, however, because an aqueous solution of methacrylic acid discharged from a methacrylic acid condensation column is directly used as an absorption solvent, problems such as lowering of the yield of methacrylic acid, the adverse effect on (over) the oxidation catalyst, the soil in a methacrylic acid absorption column and difficulty in a long-term continuous operation have not been solved at all.

Further, in British Patent No. 2,096,601, the temperature of water to be fed to the top portion of a methacrylic acid concentration column is lowered to about 3° C. so as not to allow a gas leaving from the methacrylic acid condensation column to contain methacrylic acid, and an aqueous solution phase discharged from a methacrylic acid extraction column is circulated in the reaction system as an absorption liquid to be fed to the methacrylic acid absorption column to raise the concentration of acetic acid in an aqueous solution phase discharged from the methacrylic acid extraction column, by which the absorption efficiency of methacrylic acid is raised. According to this process, because the aqueous solution phase discharged from the methacrylic acid extraction column is used in circulation, the amount of waste water can be reduced, and because the recovered methacrolein does not contain methacrylic acid and the gas leaving from the methacrylic acid condensation column does not contain high boiling point impurities, this process is free from problems related to the long-term continuous operation such as the adverse effect on the oxidation catalyst and the soil in the methacrolein absorption column. However, in order to cool the water to be fed to the top portion of the methacrylic acid condensation column, it has a problem that it requires an industrially huge amount of energy. And the methacrylic acid condensation column is required to be equipped with a sufficient number of stages and operated under strict conditions.

An object of this invention is to prevent the aforesaid problems in the conventional reaction system by recovering methacrolein substantially not containing methacrylic acid from the gas produced as a reaction product and circulating such methacrolein in the reaction system without requiring a high-performance methacrylic acid condensation column, extreme cooling or strict operational conditions.

Another object of this invention is to use an aqueous phase discharged from the methacrylic acid extraction step in circulation and resultingly decrease the amount of waste water, by which to industrially advantageously recover and re-use methacrolein.

As a result of assiduous investigations, the present inventors found that by (i) accompanying in a gas containing methacrolein discharged from the methacrylic acid condensation step with methacrylic acid and contacting the resulting gas with an aqueous phase containing methacrylic acid and acetic acid, raising the absorption efficiency of methacrolein in the methacrolein absorption step, (ii) contacting a gas containing methacrylic acid and methacrolein desorbed from the methacrolein desorption step with an aqueous phase containing acetic acid, thereby substantially removing methacrylic acid in said gas, then circulating the resulting gas containing methacrolein in the oxidation reaction system, at the same time, recovering methacrylic acid in the gas derived from the desorption step in the aqueous phase and circulating the aqueous phase in the system, (iii) circulating at least a part of an aqueous phase discharged from the methacrylic acid extraction column in the system, thereby raising the concentration of acetic acid in an aqueous phase discharged from the methacrylic acid extraction column, and circulating and using said aqueous phase as the aqueous phase described in (ii), above the aforesaid problems of the prior art could be solved.

Thus, according to this invention, there is provided, as shown in FIG. 1, a process for recovering methacrolein which comprises a reaction step (A) comprising catalytically oxidizing isobutylene, t-butanol, methacrolein, isobutyl aldehyde or isobutyric acid or a mixture thereof with a gas containing molecular oxygen in a vapor phase, a methacrylic acid condensation step (B) comprising contacting a reaction product gas obtained in the step (A) with an aqueous phase containing methacrylic acid and acetic acid, by which obtaining an aqueous solution of methacrylic acid, a methacrylic acid extraction step (C) comprising extracting methacrylic acid from the aqueous solution of methacrylic acid obtained in the step (B) using a saturated hydrocarbon having 6 to 9 carbon atoms as an extraction solvent into said solvent and separating the extracted methacrylic acid to a solvent phase and an aqueous phase containing acetic acid, a methacrolein recovery step (D) comprising contacting a gas containing methacrolein and methacrylic acid discharged from the step (B) with an aqueous phase containing methacrylic acid and acetic acid, by which recovering methacrolein and methacrylic acid contained in said gas into said aqueous phase, a methacrolein desorption step (E) comprising contacting an aqueous phase containing methacrylic acid, acetic acid and methacrolein discharged from the step (D) with a gas containing molecular oxygen, by which desorbing methacrolein, and a methacrylic acid recovery step (F) comprising contacting a gas containing methacrylic acid and methacrolein desorbed from the step (E) with an aqueous phase containing acetic acid, by which obtaining a gas containing methacrolein, at the same time, recovering methacrylic acid into said aqueous phase, characterized by circulating an aqueous phase containing acetic acid discharged from the methacrylic acid extraction step (C) in the methacrylic acid recovery step (F), circulating an aqueous phase containing methacrylic acid and acetic acid discharged from the methacrolein desorption step (E) in the methacrylic acid condensation step (B) and/or the methacrolein recovery step (D) and circulating a gas containing methacrolein discharged from the methacrylic acid recovery step (F) in the reaction step (A).

BRIEF DESCRIPTION OF DRAWING

In the accompanying drawings.

Referring to FIG. 2, the process of this invention will be specifically explained as follows.

The reaction step (A) is a step wherein isobutylene and the like are subjected to a catalytic oxidation reaction with a gas containing molecular oxygen. Examples of isobutylene and the like include isobutylene, t-butanol, methacrolein, isobutyl aldehyde or isobutyric acid or a mixture thereof. In this invention, a gas containing methacrolein discharged from a methacrolein desorption step (E) of which mention will be made later is circulated in the reaction step (A) and subjected to a catalytic oxidation reaction. The amount of molecular oxygen used vis.a.vis isobutylene and the like varies depending on the material, but ordinarily the range of 0.5 to 20 mole times is preferable, and the feed material gas may contain an inert gas such as nitrogen gas, carbon dioxide gas and a hydrocarbon. The reaction temperature varies depending on the catalyst used, but it is ordinarily 200° to 500° C., preferably 250° to 450° C. Ordinarily, the material gas is fed at a space velocity of 100 to 8,000 $hr^{-1}$ (STP), preferably at 300 to 5,000 $hr^{-1}$ (STP). The reaction may be carried out on any one of a fixed bed, a fluidized bed and a moving bed.

Figure 1:
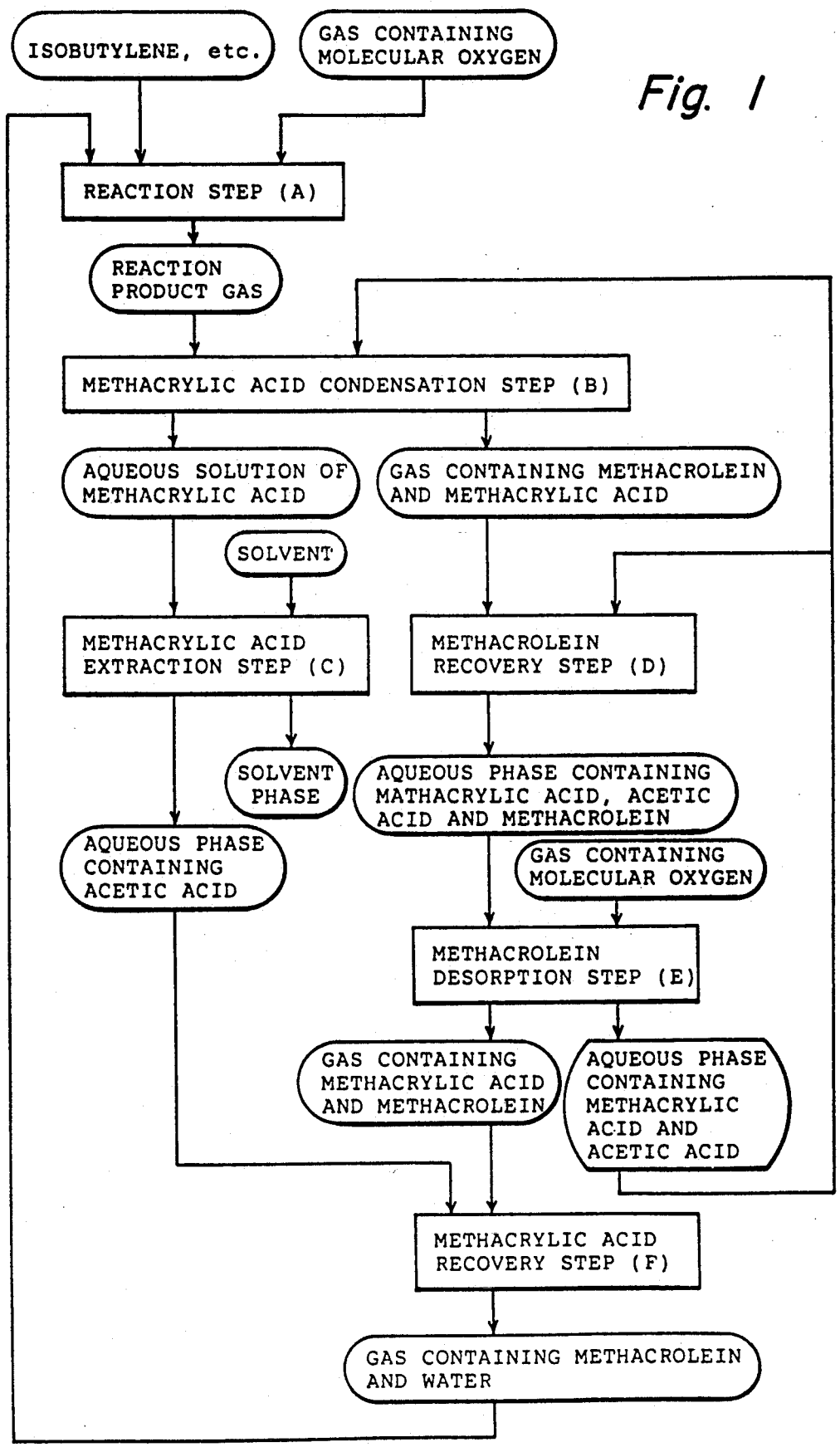
FIG. 1 is a flow sheet illustrating the gist of what is mentioned above.
Figure 2:
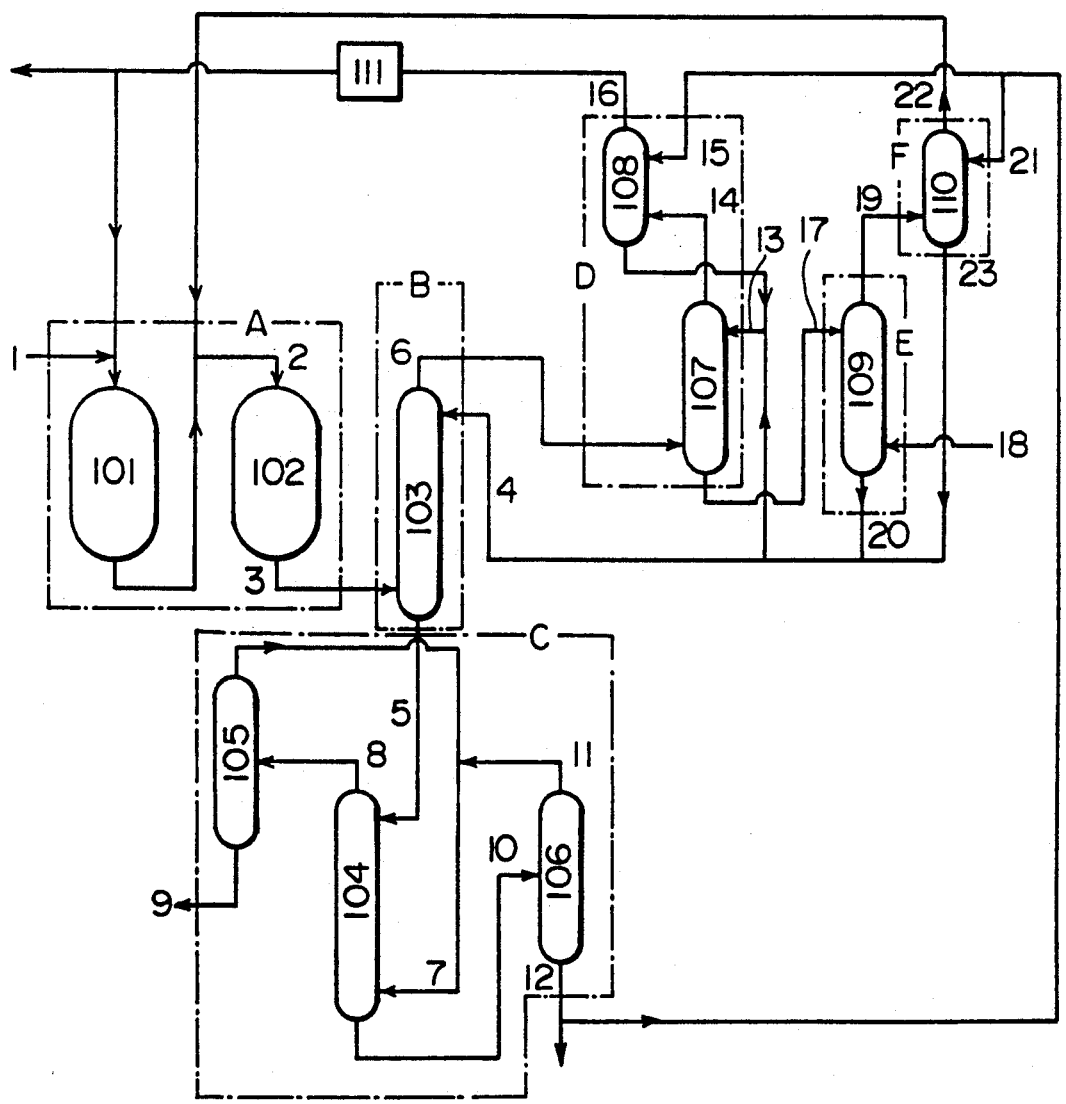
FIG. 2 is a diagram showing one preferred embodiment of this invention.

In the embodiment shown in FIG. 2, the reaction step (A) consists of a first reactor 101 mainly subjecting isobutylene and the like to an oxidation reaction to thereby obtain methacrolein and a second reactor 102 mainly subjecting methacrolein to an oxidation reaction to thereby obtain methacrylic acid. Through a line 1, the material gas containing isobutylene and the like and molecular oxygen is fed to the first reactor 101, and through a line 22, a gas containing methacrolein discharged from a methacrylic acid recovery step (F) of which mention will be made later is fed to the second reactor 102.

The methacrylic acid condensation step (B) is a step of contacting a gas obtained as a reaction product in the reaction step (A) with an aqueous phase containing methacrylic acid and acetic acid to obtain an aqueous solution of methacrylic acid. Because in this invention, in order to condense methacrylic acid in a gas produced as a reaction product, said gas is brought into contact with an aqueous phase containing methacrylic acid and acetic acid, methacrylic acid is well absorbed into the aqueous phase and a condensation step is easily carried out. When the concentrations of methacrylic acid and acetic acid in said aqueous phase are too low, the absorption of methacrylic acid becomes inadequate. Accordingly, it is preferable that the concentration of methacrylic acid is within the range of 10 to 30% by weight, and the concentration of acetic acid is within the range of 2 to 10% by weight. As an aqueous phase containing methacrylic acid and acetic acid, an aqueous phase discharged from the methacrolein desorption step (E) of which mention will be made later is suitably used. An aqueous phase discharged from the methacrylic acid extraction step (C) or the methacrylic acid recovery step (F) of which mention will be made later may be used after the concentration of methacrylic acid and the concentration of acetic acid both contained in the aqueous phase are properly adjusted.

In this invention, methacrylic acid in a gas produced as a reaction product is not completely condensed, and in a gas discharged from the methacrylic acid condensation step (B), methacrylic acid is contained together with methacrolein. This is to raise the absorption efficiency of methacrolein and to facilitate the recovery in the methacrolein recovery step (D) of which mention will be made later. The concentration of methacrylic acid in a gas discharged from the methacrylic acid condensation step (B) is preferably within the range of 2 to 5% by weight. As such, in the methacrylic acid condensation step (B) of this invention, to condense methacrylic acid in a gas produced as a reaction product, an aqueous phase well absorbing methacrylic acid is used, in addition, methacrylic acid is not completely condensed, which preclude the necessity of using an especially multi-stage methacrylic acid condensation column, or extreme cooling of an aqueous phase to be fed and enable the operator to industrially advantageously obtain an aqueous solution of methacrylic acid.

In the embodiment shown in FIG. 2, the methacrylic acid condensation step (B) mainly comprises a methacrylic acid condensation column 103. The gas obtained as a reaction product is fed to the condensation column 103 from the lower portion thereof via a line 3, while an aqueous phase containing methacrylic acid and acetic acid discharged from the methacrolein desorption column 109 and/or the methacrylic acid recovery column 110, of which mention will be made later is fed to the condensation column 103 from the upper portion thereof via a line 4 to have the two make a countercurrent (head-on) contact, whereby methacrylic acid in the gas is caused to be absorbed into the aqueous phase.

The methacrylic acid extraction step (C) is a step comprising extracting methacrylic acid from an aqueous solution of methacrylic acid obtained in the methacrylic acid condensation step (B) using an extraction solvent, into which methacrylic acid is extracted, where the extracted methacrylic acid is separated to a solvent phase and an aqueous phase. In the step (C), equipment for treating the solvent phase with such means as distillation for separating methacrylic acid, further treating the aqueous phase by such means as distillation to ensure the sufficient removal of the solvent and removing the scum appearing on the surface of the solvent produced by a high-boiling point by-product by such means as filtration in order to use the resulting methacrylic acid in circulation is ordinarily provided.

As the extraction solvent in said methacrylic acid extraction step (C), a saturated hydrocarbon having 6 to 9 carbon atoms is used.

As mentioned above or will be mentioned later, in concomitance with circulation of substances discharged from the respective steps in the reaction system, when the solvent is mixed in the reaction system, the catalyst is occasionally poisoned by the solvent and lowered in its performance, however, the saturated hydrocarbon having 6 to 9 carbon atoms does not adversely affect the reaction steps. Accordingly, such hydrocarbon can be preferably used. In addition, when a saturated hydrocarbon having 6 to 9 carbon atoms is used as an extraction solvent, acetic acid is resultingly well distributed in the aqueous phase, with the result that the concentration of acetic acid in the aqueous phase discharged from the methacrylic acid extraction step (C) is elevated. Heretofore, an aqueous phase from which methacrylic acid is already extracted has been discarded as waste water. However, in this invention, the concentration of acetic acid in said aqueous phase is elevated to raise the absorption power of methacrylic acid, and said aqueous phase is, instead of being discarded as waste water, circulated in the methacrylic acid recovery step (F) of which mention will be made later and effectively used for the recovery of methacrylic acid mixed in the gas containing methacrolein. Accordingly, the amount of waste water is decreased. Specific examples of a saturated hydrocarbon having 6 to 9 carbon atoms include linear, branched or alicyclic hexane, heptane, octane and nonane that may be used singly or in combination. Further, a mixed solvent comprising these hydrocarbons and a lower ester such as methyl methacrylate may be used as well. When saturated hydrocarbons having 6 to 9 carbon atoms are used singly or in combination, the weight ratio thereof to an aqueous solution of methacrylic acid is preferably 0.4 to 4 times. When said hydrocarbon is used in the form of a mixed solvent with a methacrylic acid ester, the ratio of the hydrocarbon based on the methacrylic acid ester is preferably at least 50% by weight.

In the embodiment shown in FIG. 2, the methacrylic acid extraction step (C) mainly comprises a methacrylic acid extraction column 104. An aqueous solution of methacrylic acid discharged from the bottom portion of the methacrylic acid condensation column 103 is introduced via a line 5 to the extraction column 104 from the upper portion thereof. On the other hand, the solvent for extraction of methacrylic acid is fed to the extraction column 104 from the lower portion thereof via a line 7. The two makes a countercurrent (head-on) contact inside the extraction column 104, where methacrylic acid is extracted by a solvent phase and withdrawn via a line 8, and an aqueous phase is withdrawn via a line 10. In the embodiment shown in FIG. 2, the solvent phase after the extraction is distilled in a solvent separation column 105 where the solvent is separated and recovered, and the recovered solvent is used in circulation in the methacrylic acid extraction column 104, while crude methacrylic acid is withdrawn via a line 9 and used per se as a material for esterification or further refined to give a methacrylic acid product. The aqueous phase after the extraction of methacrylic acid is introduced via the line 10 to a solvent recovery column 106, where it is distilled. The solvent recovered by distillation is fed to the methacrylic acid extraction column 104 via lines 11 and 7, where the aqueous phase which is the residue of distillation is withdrawn via a line 12.

The methacrolein recovery step (D) is a step comprising contacting a gas containing methacrolein and methacrylic acid discharged from the methacrylic acid condensation step (B) with an aqueous phase containing methacrylic acid and acetic acid, thereby recovering methacrolein and methacrylic acid in said gas into the aqueous phase. In this invention, the gas discharged from the methacrylic acid condensation step (B) contains methacrylic acid besides methacrolein, and the aqueous phase which is caused to contact said gas contains methacrylic acid and acetic acid. Accordingly, in concomitance with the recovery of methacrylic acid in the gas into the aqueous phase, the absorption efficiency of methacrolein increases and the recovery of methacrolein and methacrylic acid in the gas is effectively carried out. When the concentrations of methacrylic acid and acetic acid in the aqueous phase used containing methacrylic acid and acetic acid are too low, the absorption of methacrolein becomes inadequate, and when they are too high, on the other hand, methacrolein becomes unlikely to be desorbed in the subsequent methacrolein desorption step (E). Accordingly, it,.is preferable that the concentration of methacrylic acid in said aqueous phase is within the range of 10 to 30% by weight, and the concentration of acetic acid in said aqueous phase is within the range of 2 to 10% by weight. As said aqueous phase, an aqueous phase containing methacrylic acid and acetic acid discharged from the methacrolein desorption step (E) of which mention will be made later may be suitably used. The use of aqueous phases discharged from the methacrylic acid recovery step (E) and the methacrylic acid extraction step (C) after being adjusted of these concentrations is also convenient because the resulting aqueous phases are capable of decreasing the amount of waste water. Contacting of a gas discharged from the methacrolein recovery step (D) with water having small contents of methacrylic acid and acetic acid and thereby adequately absorbing methacrolein and methacrylic acid in said gas into the aqueous phase is also a preferable method.

In the case of the embodiment shown in FIG. 2, the methacrolein recovery step (D) mainly comprises a first methacrolein absorption column 107 and a second methacrolein absorption column 108. A gas discharged from the methacrylic acid condensation column 103 is fed to the first absorption column 107 from the lower portion thereof via a line 6, while aqueous phases containing methacrylic acid and acetic acid, respectively discharged from the methacrolein desorption step (E) and the second absorption column 108 are fed to the first absorption column 107 from the upper portion thereof via a line 13, then the two are brought into contact inside the first absorption column, thereby methacrolein, etc. are recovered into the aqueous phase.

In order to further recover a small amount of the residual methacrolein in a gas discharged from the first methacrolein absorption column 107, said gas is fed to the second methacrolein absorption column 108 at the lower portion thereof via a line 14, while part of an aqueous phase discharged from the solvent recovery column 106 is fed to the second absorption column 108 from the upper portion thereof via a line 15 to have the two contact, thereby methacrolein is adequately recovered into the aqueous phase, and methacrolein thus recovered is fed to the first absorption column 107. The gas after removed of methacrolein is withdrawn from the top portion of the second absorption column 108 via a line 16 and forwarded to a waste gas combustor 111, where it is disposed of by combustion, then it is used as a diluted gas for the first reactor 101, and the remnant is released into the atmosphere. As another embodiment, the gas subjected to disposal by combustion in the waste gas combustor 111 may be used as a diluted gas for the second reactor 102 or a gas for desorption of methacrolein in the methacrolein desorption column 109.

The methacrolein desorption step (E) is a step comprising contacting an aqueous phase containing methacrylic acid, acetic acid and methacrolein discharged from the aforesaid methacrolein recovery step (D) with a gas containing molecular oxygen, thereby desorbing methacrolein. As said gas containing molecular oxygen, air and a gas after being subjected to a disposal by combustion in said combustor 111 are used. In this invention, an aqueous phase containing methacrylic acid and acetic acid after desorption of methacrolein discharge from the methacrolein desorption step (E) is circulated in the methacrylic acid condensation step (B) or the methacrolein recovery step (D) and having it function effectively as an absorption solvent in the respective steps to simultaneously cut the amount of waste water. In the methacrolein desorption step (E), the amount of an aqueous phase containing acetic acid after extraction of methacrylic acid fed to the methacrylic acid recovery section based on the amount of a gas with which it is brought into contact in said recovery section is ordinarily within the range of 0.05 to 5 times by weight, and especially the range of 0.1 to 2 times by weight is preferable.

In the case of the embodiment shown in FIG. 2, the methacrolein desorption step (E) mainly comprises a first methacrolein desorption column 109. An aqueous phase containing methacrylic acid, acetic acid and methacrolein derived from the first methacrolein absorption column 107 is fed to the methacrolein desorption column 109 from the upper portion thereof via a line 17, which makes a countercurrent (head-on) contact with air fed from the lower portion of said column 109 via a line 18 inside said column 109, and a gas containing methacrolein desorbed from said aqueous phase is fed from the top portion of said column 109 via a line 19 to the subsequent methacrylic acid recovery column 110. On the other hand, an aqueous phase containing methacrylic acid and acetic acid after desorption of methacrolein is discharged via a line 20 from the bottom portion of the methacrylic acid recovery column 110, and fed to the methacrylic acid condensation column 103 and/or the first methacrolein absorption column 107.

The methacrylic acid recovery step (F) is a step comprising contacting a gas containing methacrylic acid and methacrolein discharged from the methacrolein desorption step (E) with an aqueous phase containing acetic acid, thereby obtaining a gas containing methacrolein, and recovering methacrylic acid into said aqueous phase. The gas containing methacrolein discharged from the methacrolein desorption step (E) contains methacrylic acid mixed therein, and when said gas is circulated per se in the reaction step (A), it possesses problems like lowering of the yield and adverse effect on the oxidation catalyst. However, in this invention, by contacting the gas desorbed from the methacrolein desorption step (E) with an aqueous phase containing acetic acid having a high absorption efficiency of methacrylic acid in the methacrylic acid recovery step (F), methacrylic acid is recovered and circulates a gas containing methacrolein but free from methacrylic acid in the reaction step (A). On the other hand, methacrylic acid absorbed into the aqueous phase and recovered is not lost in vain, but contributes to the improvement in the yield when said aqueous phase is properly circulated in the methacrylic acid condensation step (B) and the methacrolein recovery step (D). As an aqueous phase containing acetic acid in the methacrylic acid recovery step (F), an aqueous phase containing acetic acid discharged from the methacrylic acid extraction step (C) is used.

In the case of the embodiment shown in FIG. 2, the methacrylic acid recovery step (F) mainly comprises a methacrylic acid recovery column 110. To the methacrylic acid recovery column 110, a gas containing methacrolein is fed via a line 19 from the top portion of the methacrylic acid desorption column 109, while an aqueous phase containing acetic acid is fed via a line 21 from the solvent recovery column 106. From the top portion of the methacrylic acid recovery column 110, a gas containing methacrolein but free from methacrylic acid is fed via a line 22 to the second reactor 102, and the aqueous phase having absorbed methacrylic acid in said column 110 is fed via a line 23 to the methacrylic acid condensation column 103 or the first methacrolein absorption column 107.

In the embodiment shown in FIG. 2, partial change of the foregoing setup in which the aforesaid methacrylic acid recovery column 110 is omitted and to make up for the omission, a methacrylic acid recovery section is provided on the top portion of the methacrolein desorption column 109 and having the one column play a dual role as the methacrolein desorption step (E) and as the methacrylic acid recovery step (F) is perfectly admissible.

Hereinbelow, this invention will be more specifically explained by way of examples.

EXAMPLES

The apparatus of the embodiment shown in FIG. 2 was used.

Isobutylene and a gas containing molecular oxygen were introduced from the line 1 to the first reactor 101 packed with a molybdenum-type composite oxide. Separately, recovered methacrolein was introduced from the line 22 to the second reactor 102 packed with a heteropoly acid-type compound of the molybdenum-phosphoric acid series, and a two-stage oxidation reaction was carried out to give a gas produced as a reaction product from the lower portion of the second reactor 102. Said gas produced as a reaction product was supplied via the line 3 to the methacrylic acid condensation column 108 having an inner diameter of 100 mm and a height of 3,000 mm packed with porcelain Raschig rings, while the bottoms of the methacrolein desorption column 109 was supplied via the line 4 to said condensation column 103 from the upper portion thereof, the two were caused to make a countercurrent (head-on) contact at the column top temperature of 65° to 70° C., thereby quenching the gas and simultaneously absorbing methacrylic acid in the gas into an aqueous phase, whereby an aqueous solution of methacrylic acid was obtained from the bottom portion of the condensation column 103.

Subsequently, said aqueous solution of methacrylic acid was supplied via the line 5 to a rotating disk column having a column diameter of 50 mm and a height of 1,800 mm constituting the methacrylic acid extraction column 104 from the upper portion thereof, while n-heptane was supplied via the line 7 to the extraction column 104 from the lower portion thereof, the two were brought into contact, whereby the extraction of methacrylic acid was carried out at room temperature under atmospheric pressure. An n-heptane phase containing methacrylic acid after the extraction was withdrawn from the upper portion of the extraction column 104, introduced to the solvent separation column 105 via the line 8, where the n-heptane phase was distilled, n-heptane was recovered from the column top of the solvent separation column 105 and used in circulation in the methacrylic acid extraction column 104, while on the other hand, crude methacrylic acid was obtained from the column bottom of the solvent separation column 105. On the other hand, bottoms obtained from the lower portion of the extraction column 104 was introduced via the line 10 to the solvent recovery column 106, where it was distilled, n-heptane was recovered from the column top and used in circulation in the methacrylic acid extraction column 104. On the other hand, an aqueous phase containing acetic acid was withdrawn from the column bottom of the solvent recovery column 106 via the line 12.

On the other hand, a gas discharged from the column top of the methacrylic acid condensation column 103 was supplied via the line 6 to the first methacrolein absorption column 107 having an inner diameter of 100 mm and a height of 6,000 mm packed with porcelain Raschig rings from the lower portion thereof. The methacrolein from the bottom of the methacrylic desorption column 109 was cooled to 5° C. and supplied via line 13 to the upper portion of methacrolein absorption column 107. A gas discharged from the column top of the first methacrolein absorption column 107 was supplied via the line 14 to the second methacrolein absorption column 108 having an inner diameter of 100 mm and a height of 6,000 mm packed with porcelain Raschig rings from the lower portion thereof, while an aqueous phase containing acetic acid discharged from the solvent recovery column 106 after being subjected to filtration was supplied via the line 15 to said absorption column 109 from the upper portion thereof to bring the two into contact. A waste gas discharged from the absorption column 108 was introduced via the line 16 to a waste gas combustor 111 by the catalyst, where it was burned, and part of the gas after combustion was passed into the first reactor 101, where it was re-utilized.

On the other hand, an aqueous phase containing methacrylic acid, acetic acid and methacrolein discharged from the first methacrolein absorption column 107 was supplied via the line 17 to the methacrolein desorption column 109 having an inner diameter of 50 mm and a height of 8,000 mm packed with porcelain Raschig rings, where methacrolein was desorbed at the column top temperature of 65° to 70° C. Further, a gas discharged from the column top of said desorption column 109 was supplied via the line 19 to the methacrylic acid recovery column 110 having an inner diameter of 50 mm and a height of 5,000 mm packed with porcelain Raschig rings from the lower portion thereof, while an aqueous phase containing acetic acid discharged from the solvent recovery column 106 after being treated by filtration was introduced via the line 21 to said recovery column 110 from the upper portion thereof to contact the two, thereby methacrylic acid in the gas was recovered. The bottoms of the methacrylic acid recovery column 110 was withdrawn via the line 23, mixed with the bottom of the methacrylic acid desorption column 109, and the resulting mixture was circulated in the methacrolein absorption column 107 and the methacrylic acid condensation column 103.

Still on the other hand, a gas containing methacrolein and water discharged from the column top of the methacrylic acid recovery column 110 was circulated via the line 22 into the second reactor 102.

The entire set of the reactors, columns and lines were consecutively operated for 100 days. During the period, the operations were very stable, and pressure drops at the reactors hardly changed throughout the entire period of before, during and after the consecutive driving operations. The flow rates (kg/hr) and compositions (% by weight) at the respective sections during the driving (operations) are shown in Table-1.

as an absorption liquid of the methacrolein absorption column 107.

As a result, a gas containing methacrolein discharged from the column top of the methacrylic acid condensation column 103 hardly contained methacrylic acid, and a gas containing the recovered methacrolein discharged from the methacrolein desorption column 109 and circulated in the second reactor 102 also hardly contained methacrylic acid. However, in the methacrolein absorption column 107, clogging was produced by a polymer and so forth, resulted in gradual increase of the pressure drop, which compelled suspension of the operation on the 90th day since the initiation of the operation for washing the inside of the column 107.

From the fact mentioned above, it can be said that the process of this comparative example does not keep the long-term consecutive driving operations and cannot be adopted as an industrial process for the production as such.

What is claimed is:

1. A process for producing methacrylic acid which comprises a reaction step (A) comprising catalytically oxidizing isobutylene, t-butanol, methacrolein, isobutyl aldehyde or isobutyric acid or a mixture thereof with a gas containing molecular oxygen in a vapor phase, thereby forming a reaction product gas (a), a methacrylic acid condensation step (B) comprising contacting the reaction product gas (a) obtained in step (A) with an aqueous phase (b1) containing methacrylic acid

TABLE 1

| Line | 1 | 2 | 3 | 5 | 6 | 12 | 13 | 15 | 16 | 19 | 21 | 22 |
|---|---|---|---|---|---|---|---|---|---|---|---|---|
| Composition (% by weight) | | | | | | | | | | | | |
| Isobutylene | 9.5 | 0.1 | | | | | | | | | | |
| Methacrolein | | 7.0 | 1.3 | 0.1 | 1.3 | | | | 0.03 | 6.7 | | 6.7 |
| Methacrylic acid | | 0.4 | 5.7 | 36.3 | 4.0 | 0.6 | 18.6 | 0.6 | 0.04 | 2.3 | 0.6 | 0.6 |
| Acetic acid | | 0.4 | 1.2 | 9.3 | 0.8 | 14.6 | 4.8 | 14.6 | 0.1 | 0.25 | 14.6 | 1.1 |
| Acrylic acid | | 0.03 | 0.1 | 0.7 | 0.1 | 1.1 | 0.4 | 1.1 | | 0.02 | 1.1 | 0.1 |
| Water | 4.0 | 5.3 | 7.1 | 51.3 | 15.2 | 80.0 | 76.2 | 80.0 | 0.5 | 9.7 | 80.0 | 9.1 |
| An inorganic gas | 86.5 | 85.3 | 84.2 | | 78.7 | | | | 99.4 | 81.0 | | 82.5 |
| Others | | 0.5 | 0.4 | 2.3 | | 3.7 | | 3.7 | | | 3.7 | |
| Flow rate (kg/hr) | 3.2 | 5.5 | 5.5 | 0.9 | 5.9 | 0.5 | 12.0 | 0.1 | 3.6 | 1.1 | 0.1 | 1.1 |

COMPARATIVE EXAMPLE 1

Example was repeated except that the methacrylic acid recovery column 110 was omitted and recovered methacrolein discharged from the methacrolein desorption column 109 was circulated in the second reactor 102.

The entire set of the reactors, columns and lines were consecutively operated for 100 days as in the case of Example. During the period, the operations were stable. However, in the recovered methacrolein circulated in the second reactor 102, 2.3% by weight of methacrylic acid was contained and the pressure drop at the reactor increased to some extent after the consecutive driving operations. These facts made one wonder if something was wrong with the process of this comparative example for a long-term consecutive driving operations.

COMPARATIVE EXAMPLE 2

The operation was performed as in Example except an aqueous phase of bottom of the solvent recovery column 106 was supplied to the top of methacrylic acid condensation column 103, the aqueous phase was maintained a 5° C. after filtration and part of the bottoms of the methacrylic acid condensation column 103 was used and acetic acid, thereby obtaining an aqueous solution (b2) of methacrylic acid and a gas phase (b3) containing methacrolein and 2 to 5% by weight of methacrylic acid, a methacrylic acid extraction step (C) comprising extracting methacrylic acid from the aqueous solution (b2) of methacrylic acid obtained in step (B), into an extraction solvent comprising a saturated hydrocarbon having 6 to 9 carbon atoms thereby forming a solvent phase (c1) containing methacrylic acid and an aqueous phase (c2) containing acetic acid, a methacrolein recovery step (D) comprising contacting the gas phase (b3) containing methacrolein and methacrylic acid discharged from step (B) with an aqueous phase (d1) containing methacrylic acid and acetic acid, thereby transferring methacrolein and methacrylic acid contained in said gas phase (b3) into said aqueous phase (d), thereby forming an aqueous phase (d2) containing acetic acid, methacrylic acid and methacrolein, a methacrolein desorption step (E) comprising contacting the aqueous phase (d2) containing methacrylic acid, acetic acid and methacrolein discharged from step (D) with a gas containing molecular oxygen, thereby desorbing methacrolein and methacrylic acid into a gas phase (e1) and forming an aqueous phase (e2) containing methacrylic acid and acetic acid, and a methacrylic acid recovery step (F) comprising contacting said gas phase (e1) containing methacrylic acid and methacrolein desorbed from step (E) with said aqueous phase (c2) containing acetic acid discharged from the methacrylic extraction step (C), thereby obtaining a gas phase (f) containing methacrolein, and at the same time, recovering methacrylic acid into said aqueous phase (c2), said process further comprising circulating said aqueous phase (e2) containing methacrylic acid and acetic acid discharged from the methacrolein desorption step (E) to both the methacrylic acid condensation step (B) and the methacrolein recovery step (D), and circulating a gas phase (f) containing methacrolein discharged from the methacrylic acid recovery step (F) to the reaction step (A).

2. The process of claim 1 wherein the concentration of methacrylic acid in the gas discharged from the methacrylic acid condensation step (B) is 2 to 5% by weight.

3. The process of claim 1 wherein the concentration of acetic acid in the aqueous phase containing acetic acid used in the methacrylic acid recovery step (F) is 10 to 15% by weight.

4. The process of claim 2 wherein the concentration of acetic acid in the aqueous phase containing acetic acid used in the methacrylic acid recovery step (F) is 10 to 15% by weight.

* * * * *